United States Patent [19]

Klein et al.

[11] Patent Number: 5,258,398
[45] Date of Patent: Nov. 2, 1993

[54] ANTITHROMBOTIC DIAMINOALKANOIC ACID DERIVATIVES

[75] Inventors: Scott I. Klein, Montclair; Bruce F. Molino, Hatfield, both of Pa.

[73] Assignee: Rhone-Poulenc Rorer Pharmaceuticals Inc., Collegeville, Pa.

[21] Appl. No.: 808,400

[22] Filed: Dec. 16, 1991

[51] Int. Cl.$^5$ .......................................... A61K 31/415
[52] U.S. Cl. ..................... 514/399; 514/400; 514/419; 514/424; 514/522; 514/539; 514/542; 514/558; 514/562; 514/563; 548/495; 548/535; 548/312.1; 548/313.7; 548/314.7; 548/334.1; 554/53; 554/57; 558/414; 558/416; 560/34; 560/35; 560/37; 562/426; 562/430; 562/437; 562/439; 562/440; 562/445; 562/450; 562/560; 562/561; 562/564; 562/557
[58] Field of Search ............... 562/560, 561, 439, 440, 562/450, 426, 430, 437, 445, 564, 557; 514/539, 542, 563, 399; 548/336, 337, 341, 344, 495, 535; 554/53, 57; 558/414, 416; 560/34, 35, 37

[56] References Cited

U.S. PATENT DOCUMENTS

| | | |
|---|---|---|
| 3,364,183 | 1/1968 | Talet ............................... 562/561 |
| 4,629,736 | 12/1986 | Tsukamoto et al. . |
| 4,879,313 | 11/1989 | Tjoeng et al. . |
| 4,952,562 | 8/1990 | Klein et al. . |
| 4,992,463 | 2/1991 | Tjoeng et al. . |
| 5,037,808 | 8/1991 | Tjoeng et al. . |
| 5,053,393 | 10/1991 | Tjoeng et al. . |

OTHER PUBLICATIONS

Chemistry of the Amino Acids, vol. 1, pp. 3-8, (1961), Greenstein and Winitz, Nomenclature, Structure, and Occurrence of Amino Acids, English Original.
Annalen; vol. 670; 1963, pp. 31-47, Lingens and Hankwitz, Synthese von Acetaminomethylen-bernsteinsaure und Derivaten des Formyl-bernsteinsaure-dimeth, Statement of Relevance.
Chemical Society of Japan; Chem. Letts.; No. 10; pp. 1821-1824; 1989, Shimohigashi, Kodama, Waki and Costa, 2-Substituted gem-Diamines Derived from Amino Acid Amides. Their Applications to Cross-linking in Peptide, English Original.
J. Med. Chem., 1989, 32, 2331-2339, Rodriguez, Galas, Lignon, Mendre, Laur and Aumelas, Synthesis and Biological Activity of Some Partially Modified Retro-Inverso Analogues of Cholecystokinin, English Original.
J. Med. Chem. 1987, 30, 758-763, Rodriguez, Dubreuil, Bali and Martinez, Synthesis and Biological Activity of Partially Modified Retro-Inverso Pseudopeptide Derivatives of the C-Terminal, English Original.
Chemical Abstracts, vol. 59, No. 8: 8650g, Oct. 14, 1963, Degutis, J., Jodelyte, A. and Sukeliene, D., New Synthesis of p-[bis(2-chloroethyl)amino]-β-phenylpropionic Acid and Its Derivatives, English Original.

*Primary Examiner*—Michael L. Shippen
*Attorney, Agent, or Firm*—Paul R. Darkes; Martin F. Savitzky

[57] ABSTRACT

This invention relates to novel diaminoalkanoic acid derivatives that inhibit platelet aggregation and thrombus formation in mammalian blood thereby being useful in the prevention and treatment of thrombosis associated with disease states such as myocardial infarction, stroke, peripheral arterial disease and disseminated intravascular coagulation, to pharmaceutical compositions including such compounds, and to their use in inhibiting thrombus formation and platelet aggregation in mammals.

28 Claims, No Drawings

ANTITHROMBOTIC DIAMINOALKANOIC ACID DERIVATIVES

BACKGROUND OF INVENTION

1. Field of the Invention

This invention relates to compounds having antithrombotic activity. More particularly, the invention relates to novel diaminoalkanoic acid derivatives that inhibit platelet aggregation and thrombus formation in mammalian blood. These compounds are useful in the prevention and treatment of thrombosis associated with disease states such as myocardial infarction, stroke, peripheral arterial disease and disseminated intravascular coagulation.

Haemostasis, the biochemistry of blood coagulation, is an extremely complex and as yet not completely understood phenomena whereby normal whole blood and body tissue spontaneously arrest bleeding from injured blood vessels. Effective haemostasis requires the combined activity of vascular, platelet and plasma factors as well as a controlling mechanism to prevent excessive clotting. Defects, deficiencies, or excesses of any of these components can lead to hemorrhagic or thrombotic consequences.

Platelet adhesion, spreading and aggregation on extracellular matrices are central events in thrombus formation. These events are mediated by a family of platelet adhesive glycoproteins, i.e., fibrinogen, fibronectin, and von Willebrand factor. Fibrinogen is a co-factor for platelet aggregation, fibronectin supports platelet attachments and spreading reactions, and von Willebrand factor is important in platelet attachment to and spreading on subendothelial matrices. The binding sites for fibrinogen, fibronectin and von Willebrand factor have been located on the platelet membrane glycoprotein complex IIb/IIIa.

Adhesive glycoproteins, like fibrinogen, do not bind with normal resting platelets. However, when a platelet is activated with an agonist such as thrombin or adenosine diphosphate, the platelet changes its shape, perhaps making the GPIIb/IIIa binding site accessible to fibrinogen. The novel molecules described in this invention block the fibrinogen receptor, thus inhibiting platelet aggregation and subsequent thrombus formation. Pharmaceutical agents and/or compositions possessing such an inhibiting effect are provided for the prophylaxis and treatment of thrombogenic diseases, such as myocardial infarction, stroke, peripheral arterial disease and disseminated intravascular coagulation.

2. Reported Developments

It has been observed that the presence of Arg-Gly-Asp (RGD) is necessary in fibrinogen, fibronectin and von Willebrand factor for their interaction with the cell surface receptor (Ruoslahti E., Pierschbacher, *Cell* 1986, 44, 517-18). Two other amino acid sequences also seem to take part in the platelet attachment function of fibrinogen, namely, the Gly-Pro-Arg sequence, and the dodecapeptide, His-His-Leu-Gly-Gly-Ala-Lys-Gln-Ala-Gly-Asp-Val sequence, small synthetic peptides containing the RGD or dodecapeptide have been shown to bind to the platelet GPIIb/IIIa receptor and competitively inhibit binding of fibrinogen, fibronectin and von Willebrand factor as well as inhibit aggregation of activated platelets (Plow, et al., *Proc. Natl. Acad. Sci. USA* 1985, 82, 8057-61; Ruggeri, et al., *Proc. Natl. Acad. Sci. USA* 1986, 5708-12; Ginsberg, et al., *J. Biol. Chem.* 1985, 260, 3931-36; and Gartner, et al., *J. Biol. Chem.* 1987, 260, 11,891-94).

Indolyl compounds containing guanidinoalkanoyl- and guandinoalkenoyl-aspartyl moieties are reported to be platelet-aggregation inhibitors by Tjoeng, et al., U.S. Pat. Nos. 5,037,808 and 4,879,313.

Cyclic peptide analogues containing the moiety Gly-Asp are reported to be fibrinogen receptor antagonists in U.S. Pat. No. 5,023,233.

Peptides and pseudopeptides containing amino-, guanidino-, imidizaloyl, and/or amidino-alkanoyl, and alkenoyl moieties are reported to be antithrombotic agents in pending U.S. applications Ser. Nos. 07/677,006, 07/534,385, and 07/460,777 filed on Mar. 28, 1991, Jun. 7, 1990, and Jan. 4, 1990, respectively, as well as in U.S. Pat. No. 4,952,562, all assigned to the same assignee as the present invention.

Peptides and pseudopeptides containing amino- and guanidino-alkyl-and alkenyl-benzoyl, phenylalkanoyl, and phenylalkenoyl moieties are reported to be antithrombotic agents in pending U.S. application Ser. No. 07/475,043, filed Feb. 5, 1990, assigned to the same assignee as the present invention.

The present invention relates to novel diaminoalkanoic acid derivatives which inhibit platelet aggregation and subsequent thrombus formation.

SUMMARY OF THE INVENTION

Compounds of the present invention are described by Formula I

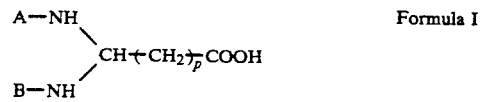

wherein:

A and B are independently alkanoyl, alkenoyl, D- or L-α-amino acyl, or X—G—(M)$_n$—
where X is

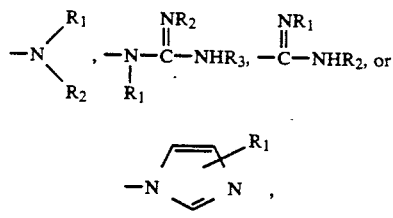

G is alkanoyl, alkenoyl, benzoyl, substituted benzoyl, phenylalkanoyl, substituted phenylalkanoyl, phenylalkenoyl, substituted phenylalkenoyl, alkyl- or alkenylbenzoyl, substituted alkyl- or alkenylbenzoyl, alkyl- or alkenylphenylalkanoyl, substituted alkyl- or alkenylphenylalkanoyl, alkyl- or alkenylphenylalkenoyl, substituted alkyl- or alkenylphenylalkenoyl, or N-alkanoyl-or N-alkenoyl-D- or L-α-amino acyl, and M is $$-\underset{R_4}{\text{N}}-CH_2-\overset{O}{\overset{\|}{C}}-$$

where $R_1$, $R_2$, $R_3$, and $R_4$ are independently hydrogen or alkyl and n is 0, or 1; and p is 1, 2, or 3;
or a pharmaceutically acceptable salt thereof; provided that if G is alkanoyl, alkenoyl, or N-alkanoyl- or N-alkenoyl-D-or L-α-amino acyl, then n is 0.

Additionally, this invention relates to pharmaceutical compositions comprising such compounds, and to their use in inhibiting thrombus formation and platelet aggregation.

DETAILED DESCRIPTION OF THE INVENTION

As used above, and throughout the description of this invention, the following terms, unless otherwise indicated, shall be understood to have the following meanings:

"Alkyl" means a saturated aliphatic hydrocarbon group which may be straight or branched, or contain one or more cyclic hydrocarbon groups, and having about 1 to about 20 carbon atoms in the chain. "Branched" means that a lower alkyl group such as methyl, ethyl or propyl is attached to a linear alkyl chain. "Containing one or more cyclic hydrocarbon groups" means that the cycloalkyl groups, for example cyclohexyl or cyclopentyl, may be attached to a linear alkyl chain, or may be contained within the chain as, for example 1,2-, 1,3-, or 1,4-cyclohexylene groups. Preferred alkyl groups are lower alkyl groups, i.e., those groups having from 1 to about 12 carbons.

"Aryl" means phenyl or naphthyl.

"Alkenyl" means an alkyl group which may contain one or more double bonds which may be in the cis or trans configuration. Preferred alkenyl groups include vinyl and allyl.

"Alkanoyl" means an

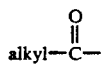

group. Preferred alkanoyl groups are those in which the alkyl group is lower alkyl.

"Alkenoyl" means an

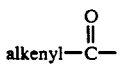

group. Preferred alkenoyl groups include those in which the alkenyl group is vinyl or allyl.

"α-amino acyl" means a synthetic or naturally occurring amino acid group. Preferred α-amino acyl groups include glycyl, alanyl, valyl, leucyl, isoleucyl, seryl, threonyl, phenylalanyl, tyrosyl, tryptophanyl, cysteyl, methionyl, prolyl, hydroxyprolyl, aspartyl, asparginyl, glutamyl, glutaminyl, histidyl, arginyl, ornithyl, and lysyl.

"Phenylalkanoyl" means a

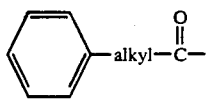

group. Preferred phenylalkanoyl groups include phenylacetyl, phenylpropanoyl, and phenylbutyryl.

"Phenylalkenoyl" means a

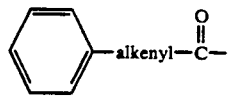

group. Preferred phenylalkenoyl groups include cinnamoyl and 4-phenyl-3-butenoyl.

"Substituted benzoyl, phenylalkanoyl, phenylalkenoyl, alkyl- or alkenylbenzoyl, alkyl- or alkenylphenylalkanoyl, and alkyl- or alkenylphenylalkenoyl" mean that the phenyl group in each of the respective groups is substituted with one or more aryl group substituents, which may be the same or different, where "aryl group substituent" includes alkyl, alkenyl, alkynyl, aryl, aralkyl, hydroxy, alkoxy, aryloxy, aralkoxy, hydroxyalkyl, alkanoyl, formyl, carboxy, alkenoyl, aroyl, halo, nitro, trihalomethyl, cyano, alkoxycarbonyl, aryloxycarbonyl, aralkoxycarbonyl, alkanoylamino, aroylamino, carbamoyl, alkylcarbamoyl, dialkylcarbamoyl, arylcarbamoyl, aralkylcarbamoyl, alkylsulfonyl, alkylsulfinyl, arylsulfonyl, arylsulfinyl, aralkylsulfonyl, aralkylsulfinyl, or -NRR' where R and R' are independently hydrogen, alkyl, aryl, or aralkyl.

A preferred class of compounds of the present invention is described by Formula I wherein G is alkanoyl, alkenoyl, benzoyl, phenylalkanoyl, phenylalkenoyl, alkyl- or alkenylbenzoyl, alkyl- or alkenylphenylalkanoyl, alkyl-or alkenylphenylalkenoyl, or N-alkanoyl- or N-alkenoyl-D- or L-α-amino acyl.

Another preferred class of compounds of the present invention is described by Formula I wherein A and B are independently D- or L-α-amino acyl.

Another preferred class of compounds of the present invention is described by Formula I wherein A and B are independently X—G—(M)$_n$—, where G is benzoyl, phenylalkanoyl, phenylalkenoyl, alkyl- or alkenylbenzoyl, alkyl- or alkenylphenylalkanoyl, alkyl- or alkenylphenylalkenoyl.

A more preferred class of compounds of the present invention is described by Formula I wherein G is alkanoyl, alkenoyl, or N-alkanoyl- or N-alkenoyl-D-or L-α-amino acyl.

A most preferred class of compounds of the present invention is described by Formula I wherein X is

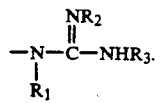

A most preferred embodiment of the present invention is described by Formula I wherein G is alkanoyl or alkenoyl.

Another most preferred embodiment of the present invention is described by Formula I wherein G is alkanoyl, alkenoyl, or N-alkanoyl- or N-alkenoyl-D-or L-α-amino acyl, and X is

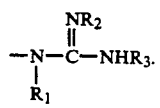

Representative compounds of the present invention include:

N,N'-bis-(8-guanidino)octanoyl-3,3-diaminopropionic acid,
(3S)-N-(8-guanidino)octanoyl-N'-(9-guanidino)nonanoyl-3,3-diaminopropionic acid,
(3R)-N-L-arginyl-N'-(8-guanidino)octanoyl-3,3-diaminopropionic acid,
N,N'-bis-(7-guanidino)heptanoyl-3,3-diaminopropionic acid,
N,N'-bis-(9-guanidino)nonanoyl-3,3-diaminopropionic acid,
(3S)-N-(7-guanidino)heptanoyl-N'-(9-guanidino)nonanoyl-3,3-diaminopropionic acid,
(3S)-N-(7-guanidino)heptanoyl-N'-(8-guanidino)octanoyl-3,3-diaminopropionic acid,
(3R)-N-(8-guanidino)octanoyl-N'-(9-guanidino)nonanoyl-3,3-diaminopropionic acid,
(3S)-N-L-arginyl-N'-(8-guanidino)octanoyl-3,3-diaminopropionic acid,
(3R)-N-(7-guanidino)heptanoyl-N'-(9-guanidino)nonanoyl-3,3-diaminopropionic acid,
(3R)-N-(7-guanidino)heptanoyl-N'-(8-guanidino)octanoyl-3,3-diaminopropionic acid,
(3R)-N-(8-guanidino)octanoyl-N'-(3-methyl)butanoyl-3,3-diaminopropionic acid,
(3S)-N-(8-guanidino)octanoyl-N'-(3-methyl)butanoyl-3,3-diaminopropionic acid,
(3R)-N-[N-[(5-guanidino)pentanoyl]-D-isoleucyl]-N'-(9-guanidino)nonanoyl-3,3-diaminopropionic acid,
(3S)-N-[N-[(5-guanidino)pentanoyl]-D-isoleucyl]-N'-(9-guanidino)nonanoyl-3,3-diaminopropionic acid,
(3R)-N-[N-[(5-guanidino)pentanoyl]-L-isoleucyl]-N'-(9-guanidino)nonanoyl-3,3-diaminopropionic acid,
(3S)-N-[N-[(5-guanidino)pentanoyl]-L-isoleucyl]-N'-(9-guanidino)nonanoyl-3,3-diaminopropionic acid, and
N,N'-bis-(8-guanidino)octanoyl-4,4-diaminobutanoic acid
and pharmaceutically acceptable salts thereof.

Compounds of the present invention contain asymmetric centers. These asymmetric centers may independently be in either the R or S configuration. The present invention comprises the individual stereoisomers and mixtures thereof.

The compounds of the present invention may be useful in the form of the free base or acid or in the form of a pharmaceutically acceptable salt thereof. All forms are within the scope of the invention.

Where the compound of the present invention is substituted with a basic moiety, acid addition salts may be formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial antithrombotic properties inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanoesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, malonate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial antithrombotic properties inherent in the free acid are not vitiated by side effects ascribable to the cations. Pharmaceutically acceptable salts within the scope of the invention are those derived from the following bases: sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

Metal salts of compounds of the present invention may be obtained by contacting a hydroxide, carbonate or similar reactive compound of the chosen metal in an aqueous solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

Compounds of this invention may be prepared in accordance with the reaction sequences described below, or can be prepared by methods known in the art. The starting materials used in the preparation of compounds of this invention are known or are commercially available, or can be prepared by known methods or by specific reaction schemes described herein.

The compounds of the present invention are available, generally, by coupling an appropriately substituted carboxylic acid to an α-amino-α-(carboxy)alkyl acetamide, wherein the carboxyl group of the acetamide is protected, to give the diamide, followed by an oxidative rearrangement of the primary amide moiety to the corresponding amine which is, in turn, coupled to another appropriately substituted carboxylic acid and deprotecting as necessary.

If it is desirable or necessary to prevent cross-reaction between chemically active substituents on the carboxylic acids or amide, the substituents may be protected by standard blocking groups which may subsequently be removed or retained, as required, by known methods to afford the desired products or intermediates (see, for example, Green, "Protective Groups in Organic Synthesis", Wiley, N.Y., 1981). Selective protection or deprotection may also be necessary or desirable to allow conversion or removal of existing substituents, or to allow subsequent reaction to afford the final desired product.

The general method of preparation of compounds of the present invention is shown in Scheme I below.

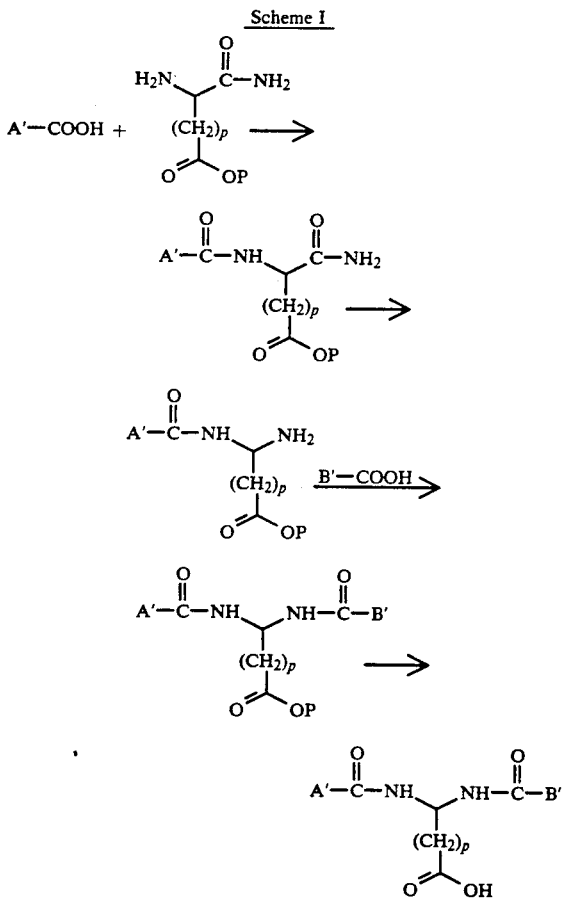

Where A'-COOH is A-OH where A is as defined hereinabove or A'-COOH is a protected derivative thereof or precursor moiety thereto, and P is a carboxylic acid protecting group.

A carboxylic acid is condensed with a protected α-amino-α-(carboxy)alkyl acetamide to prepare the corresponding diamide. Methods for preparing amides from carboxylic acids and amines are well known in the art (see, for example, M. Bodanszky, "Principles of Peptide Synthesis", Springer-Verlag, Berlin (1984)). A preferred method of preparation of the diamide is by treatment of the appropriate carboxylic acid with 1-(3-dimethylaminopropyl)-3-ethylcarbodiimide hydrochloride in the presence of triethylamine and 1-hydroxybenzotriazole in a solvent, for example dimethylformamide, followed by reaction with the appropriate amine.

The primary amide portion of the diamide is then converted to a primary amine by known methods, for example by a Hofmann rearrangement. A preferred method of effecting this rearrangement is that of Loudon, et al., *J. Org. Chem.* 1984, 49, 4272–4276, wherein the amide is treated with [I,I-bis(trifluoroacetoxy)iodo]benzene in acetonitrile to prepare the corresponding amine.

A second carboxylic acid is reacted with the resulting amine to afford the desired diamide. The carboxylic acid is then deprotected by methods known in the art, any further modification or deprotection of the A' or B' groups which is necessary or desirable being done either before or after said deprotection, to yield the desired compound of the present invention.

The present invention is further explained by the following illustrative examples.

EXAMPLE 1

Preparation of N,N'-bis-(8-guanidino)octanoyl-3,3-diaminopropionic acid

Step 1: Preparation of 8-(2-nitro)guanidinooctanoic acid

A mixture of fuming nitric acid (20 ml) and fuming sulfuric acid (12 ml) is cooled to 0° C. and 8-guanidinooctanoic acid (1 g) is added. The mixture is stirred at 0° C. for about 1 hour, then poured over ice. The pH is adjusted to >8 with concentrated ammonium hydroxide, then reacidified with glacial acetic acid. The resulting precipitate is collected by filtration, washed with cold water and dried in vacuo to give the desired product.

Step 2: Preparation of N-α-8-[(2-nitro)guanidino]octanoylaspartic acid amide β-benzyl ester To a solution of 8-(2-nitro)guanidinooctanoic acid (0.46 g) in dimethylformamide (5 ml) is added 1-(3-dimethylaminopropyl)-3-ethylcarbodiimide hydrochloride (0.36 g), 1-hydroxybenzotriazole (0.26 g) and triethylamine (0.26 ml) and the mixture stirred at room temperature for about 5 minutes. Aspartic acid amine β-benzyl ester (0.48 g) is added and the mixture stirred at room temperature for about 24 hours. The mixture is diluted with ethyl acetate and washed with water, 1N hydrochloric acid, water, saturated sodium bicarbonate solution, and water. The organic layer is dried over magnesium sulfate, filtered, and the filtrate concentrated in vacuo to give the desired product.

Step 3: Preparation of benzyl N-8-(2-nitro)-guanidinooctanoyl-3,3-diaminopropionate To a solution of iodobenzene ditrifluoroacetate (0.29 g) in acetonitrile (4 ml) and water (4 ml) is added N-α-8-[(2-nitro)guanidino]octanoylaspartic acid amide β-benzyl ester (0.3 g) and the mixture stirred at room temperature for about 6 hours. Water (50 ml) is added, followed by concentrated hydrochloric acid (1 ml) and stirring continued for 15 minutes. The mixture is washed with ether and the aqueous layer lyophilized to give the desired product as the hydrochloride salt which was used, without further treatment, for the next step.

Step 4: Preparation of benzyl N,N'-bis-[8-(2-nitro)-guanidino]octanoyl-3,3-diaminopropionate To a solution of 8-(2-nitro)guanidinooctanoic acid (0.083 g) in dimethylformamide (5 ml) is added 1-(3-dimethylaminopropyl)-3-ethylcarbodiimide hydrochloride (0.061 g), 1-hydroxybenzotriazole (0.043 g) and triethylamine (0.05 ml) and the mixture stirred at room temperature for about 5 minutes. Benzyl N-8-(2-nitro)-guanidinooctanoyl-3,3-diaminopropionate hydrochloride (0.145 g) is added and the mixture stirred at room temperature for about 24 hours. The mixture is diluted with ethyl acetate and washed with water, 1N hydrochloride acid, water, saturated sodium bicarbonate solution, and water. The organic layer is dried over magnesium sulfate, filtered, and the filtrate concentrated in vacuo to give the desired product.

Step 5: Preparation of N,N'-bis-(8-guanidino)octanoyl-3,3-diaminopropionic acid

Benzyl N,N'-bis-[8-(2-nitro)guanidino]octanoyl-3,3-diaminopropionate (0.11 g) is dissolved in methanol (20 ml) and glacial acetic acid (20 ml) and 10% palladium on carbon (0.05 g) is added and the mixture stirred under an atmosphere of hydrogen at 45 psi at room temperature for about 24 hours. The mixture is filtered and the filtrate concentrated in vacuo to remove methanol. The residue is diluted with water and washed with ethyl acetate. The aqueous layer is lyophilized and the residue purified by reverse phase HPLC, followed by lyophilization after addition of a few drops of trifluoroacetic acid, to give the desired product as the ditrifluoroacetate salt, NMR (300 MHz, $D_2O$) $\delta$5.62 (t, 1H, J=7.1 Hz), 2.98 (t, 4H, J=6.8 Hz), 2.62 (d, 2H, J=6.8 Hz), 2.04 (t, 4H, J=6.9 Hz), 1.40-1.13 (m, 20H); Mass Spec. (Low Resolution Fast Atom Bombardment (LRFAB)), (M+1)+ Cal'd: 471, Found: 471.

Using essentially the procedure of Example 1, the following compounds are prepared, as the triflouroacetate salts, from the appropriate starting materials.

EXAMPLE 2

(3S)-N-(8-guanidino)octanoyl-N'-(9-guanidino)nonanoyl-3,3-diaminopropionic acid, NMR (300 MHz, $D_2O$) $\delta$5.61 (t, 1H, J=7.0 Hz), 2.99 (t, 4H, J=6.8 Hz), 2.60 (d, 2H, J=6.7 Hz), 2.03 (t, 4H, J=7.0 Hz), 1.41-1.15 (m, 22H); M.S. (LRFAB), Cal'd: 485, Found: 485.

EXAMPLE 3

(3R)-N-L-arginyl-N'-(8-guanidino)octanoyl-3,3-diaminopropionic acid

EXAMPLE 4

N,N'-bis-(7-guanidino)heptanoyl-3,3-diaminopropionic acid, NMR (300 MHz, $D_2O$) $\delta$5.58 (t, 1H, J=6.5 Hz), 3.00 (t, 4H, J=6.8 Hz), 2.46 (d, 2H, J=6.5 Hz), 2.05 (t, 4H, J=7.0 Hz), 1.43-1.16 (m, 16H), M.S. (LRFAB), Cal'd: 443, Found: 443.

EXAMPLE 5

N,N'-bis-(9-guanidino)nonanoyl-3,3-diaminopropionic acid, NMR (300 MHz, $D_2O$) $\delta$5.65 (t, 1H, J=6.9 Hz), 2.97 (t, 4H, J=7.0 Hz), 2.66 (d, 2H, J=6.8 Hz), 2.06 (t, 4H, J=7.0 Hz), 1.39-1.13 (m, 24H), M.S. (LRFAB), Cal'd: 499, Found: 499.

EXAMPLE 6

(3S)-N-(7-guanidino)heptanoyl-N'-(9-guanidino)nonanoyl-3,3-diaminopropionic acid, NMR (300 MHz, $D_2O$) $\delta$5.60 (t, 1H, J=6.8 Hz), 2.98 (t, 4H, J=7.1 Hz), 2.55 (d, 2H, J=6.9 Hz), 2.03 (t, 4H, J=7.0 Hz), 1.39-1.12 (m, 20H), M.S. (LRFAB), Cal'd: 471, Found: 471.

EXAMPLE 7

(3S)-N-(7-guanidino)heptanoyl-N'-(8-guanidino)octanoyl-3,3-diaminopropionic acid, NMR (300 MHz, $D_2O$) $\delta$5.58 (t, 1H, J=7.0 Hz), 3.00 (t, 4H, J=6.6 Hz), 2.46 (d, 2H, J=6.4 Hz), 2.05 (t, 4H, J=6.8 Hz), 1.41-1.15 (m, 18H), M.S. (LRFAB), Cal'd: 457, Found: 457.

EXAMPLE 8

(3R)-N-(8-guanidino)octanoyl-N'-(9-guanidino)nonanoyl-3,3-diaminopropionic acid, NMR (300 MHz, $D_2O$) $\delta$5.65 (t, 1H, J=6.9 Hz), 2.99 (t, 4H, J=6.9 Hz), 2.65 (d, 2H, J=7.0 Hz), 2.05 (t, 4H, J=7.0 Hz), 1.41-1.16 (m, 22H), M.S. (LRFAB), Cal'd: 485, Found: 485.

EXAMPLE 9

(3S)-N-L-arginyl-N'-(8-guanidino)octanoyl-3,3-diaminopropionic acid, M.S. (LRFAB), Cal'd: 444, Found: 444.

EXAMPLE 10

(3R)-N-(7-guanidino)heptanoyl-N'-(9-guanidino)nonanoyl-3,3-diaminopropionic acid, NMR (300 MHz, $D_2O$) $\delta$5.64 (t, 1H, J=6.7 Hz), 2.98 (t, 4H, J=7.0 Hz), 2.65 (d, 2H, J=6.9 Hz), 2.04 (t, 4H, J=7.0 Hz), 1.40-1.14 (m, 20H), M.S. (LRFAB), Cal'd: 471, Found: 471.

EXAMPLE 11

(3R)-N-(7-guanidino)heptanoyl-N'-(8-guanidino)octanoyl-3,3-diaminopropionic acid, NMR (300 MHz, $D_2O$) $\delta$5.65 (t, 1H, J=6.7 Hz), 2.98 (t, 4H, J=7.0 Hz), 2.65 (d, 2H, 6.8 Hz), 2.04 (t, 4H, J=7.1 Hz), 1.40-1.13 (m, 18H), M.S. (LRFAB), Cal'd: 457, Found: 457.

EXAMPLE 12

(3R)-N-(8-guanidino)octanoyl-N'-(3-methyl)butanoyl-3,3-diaminopropionic acid, NMR (300 MHz, $D_2O$) $\delta$5.66 (t, 1H, J=6.7 Hz), 2.98 (t, 2H, J=6.9 Hz), 2.68 (d, 2H, 6.8 Hz), 2.03 (t, 2H, J=7.0 Hz), 1.90 (d, 2H, J=7.4), 1.82-1.78 (m, 1H), 1.40-1.12 (m, 10H), 0.72 (d, 6H, J=6.5 Hz), M.S. (LRFAB), Cal'd: 372, Found: 372.

EXAMPLE 13

(3S)-N-(8-guanidino)octanoyl-N'-(3-methyl)butanoyl-3,3-diaminopropionic acid

EXAMPLE 14

(3S)-N-[N-[(5-guanidino)pentanoyl]-D-isoleucyl]-N'-(9-guanidino)nonanoyl-3,3-diaminopropionic acid

EXAMPLE 15

(3R)-N-[N-[(5-guanidino)pentanoyl]-D-isoleucyl]-N'-(9-guanidino)nonanoyl-3,3-diaminopropionic acid, NMR (300 MHz, $D_2O$) $\delta$5.66 (t, 1H, J=6.8 Hz), 3.85 (d, 1H, J=8.0 Hz), 2.97-2.93 (m, 4H), 2.65 (d, 2H, J=6.8 Hz), 2.11 (t, 2H, J=6.9), 1.98 (t, 2H, J=7.1 Hz), 1.36–1.32 (m, 1H), 1.09–0.97 (m, 18H), 0.68–0.62 (m, 6H), M.S. (LRFAB), Cal'd: 556, Found: 556.

EXAMPLE 16

(3S)-N-[N-[(5-guanidino)pentanoyl]-L-isoleucyl]-N'-(9-guanidino)nonanoyl-3,3-diaminopropionic acid

EXAMPLE 17

(3R)-N-[N-(5-guanidino)pentanoyl]-L-isoleucyl]-N'-(9-guanidino)nonanoyl-3,3-diaminopropionic acid, NMR (300 MHz, D$_2$O) δ5.64 (t, 1H, J=6.8 Hz), 3.86 (d, 1H, J=7.9 Hz), 2.98–2.93 (m, 4H), 2.65 (d, 2H, J=6.7 Hz), 2.11 (t, 2H, J=7.0), 1.98 (t, 2H, J=7.0 Hz), 1.36–1.32 (m, 1H), 1.08–0.97 (m, 18H), 0.68–0.62 (m, 6H), M.S. (LRFAB), Cal'd: 556, Found: 556.

EXAMPLE 18

N,N'-bis-(8-guanidino)octanoyl-4,4-diaminobutanoic acid, NMR (300 MHz, D$_2$O) δ5.33 (t, 1H, J=7.3 Hz), 2.95 (t, 4H, J=6.9 Hz), 2.24 (t, 2H, J=7.1 Hz), 2.01 (t, 4H, J=7.0 Hz), 1.82 (dd, 2H, J=5.8, 12.0 Hz), 1.36–1.07 (m, 20H), M.S. (LRFAB), Cal'd: 485, Found: 485.

The compounds of the present are useful in the prevention and treatment of thrombosis associated with disease states such as myocardial infarction, stroke, peripheral arterial disease and disseminated intravascular coagulation. It is believed that the compounds exhibit such utility by virtue of their abilit to inhibit platelet aggregation and thrombus formation in mammalian blood.

The compounds of this invention can normally be administered orally or parenterally, in the treatment or prevention of thrombosis associated disease states.

The compounds of this invention may be formulate for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of platelet aggregation and thrombus inhibiting compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, they are suitably buffered, they are made isotonic with sufficient saline or glucose and sterilized by heating or microfiltration.

The dosage regimen in carrying out the method of this invention is that which insures maximum therapeutic response until improvement is obtained and thereafter the minimum effective level which gives relief. In general, the oral dose may be between about 1 mg/kg and about 200 mg/kg, and the i.v. dose about 0.1 mg/kg to about 20 mg/kg, bearing in mind, of course, that in selecting the appropriate dosage in any specific case, consideration must be given to the patient's weight, general health, age, and other factors which may influence response to the drug. The drug may be administered orally 1 to 4 times per day, preferably twice daily.

Compounds of the present invention are inhibitors of thrombus formation and platelet aggregation and as such possess therapeutic value in the prevention and treatment of thrombosis associated with certain disease states.

The effectiveness of compounds of the present invention as inhibitors of thrombus formation and platelet aggregation may be determined by the following pharmacologic tests which evaluate the inhibition of fibrinogen-mediated platelet aggregation and fibrinogen binding to thrombin-stimulated platelets by said compounds.

The Platelet Aggregation Assay is based on that described in *Blood* 66 (4), 946–952 (1985). The Fibrinogen-Binding Assay is essentially that of Ruggeri, Z. M., et al., *Proc. Natl. Acad. Sci. USA* 83, 5708–5712 (1986) and Plow, E. F., et al., *Proc. Natl. Acad. Sci., USA* 82, 8057–8061 (1985).

Platelet Aggregation Assay

Preparation of Fixed-Activated Platelets

Platelets are isolated from human platelet concentrates using the gel-filtration technique as described by Marguerie, G. A., et al., *J. Biol. Chem.* 254, 5357–5363 (1979) and Ruggeri, Z. M., et al., *J. Clin. Invest.* 72, 1–12 (1983). The platelets are suspended at a concentration of $2 \times 10^8$ cells/ml in a modified calcium-free Tyrode's buffer containing 127 mM sodium chloride, 2 mM magnesium chloride, 0.42 mM Na$_2$HPO$_4$, 11.9 mM NaHCO$_3$, 2.9 mM KCl, 5.5 mM glucose, 10 mM HEPES, at a pH of 7.35 and 0.35% human serum albumin (HSA). These washed platelets are activated by addition of human α-thrombin at a final concentration of 2 units/ml, followed by thrombin inhibitor I-2581 at a final concentration of 40 μM. To the activated platelets is added paraformaldehyde to a final concentration of 0.50% and this incubated at room temperature for 30 minutes. The fixed activated platelets are then collected by centrifugation at 650×g for 15 minutes. The platelet pellets are washed four times with the above Tyrode's-0.35% HSA buffer and resuspended to $2 \times 10^8$ cells/ml in the same buffer.

Platelet Aggregation Assay

The fixed activated platelets are incubated with a selected dose of the compound to be tested for platelet aggregation inhibition for one minute and aggregation initiated by addition of human fibrinogen to a final concentration of 250 μg/ml. A platelet aggregation profiler Model PAP-4 is used to record the platelet aggregation. The extent of inhibition of aggregation is expressed as the percentage of the rate of aggregation observed in the absence of inhibitor. $IC_{50}$, i.e., the amount of inhibitor required to reduce the aggregation rate by 50%, is then calculated for each compound (see, for example, Plow, E. F., et al., *Proc. Natl. Acad. Sci. USA* 82, 8057–8061 (1985)).

Fibrinogen-Binding Assay

Platelets are washed free of plasma constituents by the albumin density-gradient technique of Walsh, P. N., et al., *Br. J. Haematol.* 281–296 (1977), as modified by Trapani-Lombardo, V., et al., *J. Clin Invest.* 76, 1950–1958 (1985). In each experimental mixture platelets in modified Tyrode's buffer (Ruggeri, Z. M., et al., *J. Clin. Invest.* 72, 1–12 (1983)) are stimulated with human α-thrombin at 22°–25° C. for 10 minutes ($3.125 \times 10^{11}$ platelets per liter and thrombin at 0.1 NIH units/ml). Hirudin is then added at a 25-fold excess (unit/unit) for 5 minutes before addition of the $^{125}$I-labeled fibrinogen and the compound to be tested. After these additions, the final platelet count in the mixture is $1 \times 10^{11}$/liter. After incubation for an additional 30 minutes at 22°–25° C., bound and free ligand are separated by centrifuging 50 μl of the mixture through 300 μl of 20% sucrose at 12,000×g for 4 minutes. The platelet pellet is then separated from the rest of the mixture to determine platelet-bound radioactivity. Nonspecific binding is measured in mixtures containing an excess of unlabeled ligand. When binding curves are analyzed by Scatchard analysis, nonspecific binding is derived as a fitted parameter from the binding isotherm by means of a computerized program (Munson, P. J., *Methods Enzymol.* 92, 542–576 (1983)). To determine the concentration of each inhibitory compound necessary to inhibit 50% of fibrinogen binding to thrombin-stimulated platelets ($IC_{50}$), each compound is tested at 6 or more concentrations with $^{125}$I-labeled fibrinogen held at 0.176 μmol/liter (60 μg/ml). The $IC_{50}$ is derived by plotting residual fibrinogen binding against the logarithm of the sample compound's concentration.

Compounds of the present invention exhibit marked activity in the foregoing tests and are considered useful in the prevention and treatment of thrombosis associated with certain disease states. Results of testing of compounds of the present invention by the above methods are presented in the table below.

| Compound of Example | Inhibition Fibrinogen-Mediated Platelet Aggregation | Inhibition of $^{125}$I-Fibrinogen Binding to Platelet |
|---|---|---|
| 1 | 0.12 | 0.07 |
| 2 | 1.3 | — |
| 4 | 2.8 | — |
| 5 | 0.14 | — |
| 6 | 2.8 | — |
| 7 | 0.74 | — |
| 8 | 0.30 | — |
| 9 | 9.8 | 1.2 |
| 10 | 0.12 | — |
| 11 | 0.32 | — |
| 12 | 2.0 | — |
| 15 | 25 | — |
| 17 | 17.5 | — |
| 18 | >100 μM | — |

One skilled in the art will readily appreciate that the present invention is well adapted to carry out the objects and obtain the ends and advantages mentioned, as well as those inherent therein. The compounds, compositions, and methods described herein are presented as representative of the preferred embodiments, or intended to be exemplary and not intended as limitations on the scope of the present invention. Changes therein and other uses will occur to those of skill in the art which are encompassed within the spirit of the invention or defined by the scope of the appended claims.

What is claimed is:

1. A compound of the formula

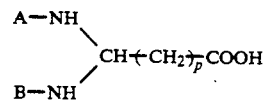

wherein:

A and B are independently alkanoyl, alkenoyl, D- or L-α-amino acyl, or X—G—(M)$_n$— where X is

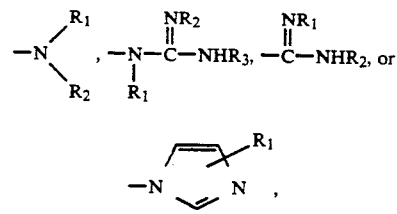

G is alkanoyl, alkenoyl, benzoyl, substituted benzoyl, phenylalkanoyl, substituted phenylalkanoyl, phenylalkenoyl, substituted phenylalkenoyl, alkyl- or alkenylbenzoyl, substituted alkyl- or alkenylbenzoyl, alkyl- or alkenylphenylalkanoyl, substituted alkyl- or alkenylphenylalkanoyl, alkyl- or alkenylphenylalkanoyl, substituted alkyl- or alkenylphenylalkanoyl, or N-alkanoyl-or N-alkenoyl-D- or L-α-amino acyl, and M is

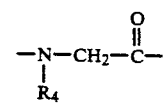

where $R_1$, $R_2$, $R_3$, and $R_4$ are independently hydrogen or alkyl and n is 0, or 1; and p is 1, 2, or 3;

where said substituted benzoyl, phenylalkanoyl, phenylalkenoyl, alkyl- or alkenylbenzoyl, alkyl- or alkenylphenylalkanoyl, and alkyl- or alkenylphenylalkenoyl contain one or more substituents selected from the group consisting of alkyl, alkenyl, alkynyl, aryl, aralkyl, hydroxy, alkoxy, aryloxy, aralkoxy, hydroxyalkyl, alkanoyl, formyl, carboxy, alkenoyl, aroyl, halo, nitro, trihalomethyl, cyano, alkoxycarbonyl, aryloxycarbonyl, aralkoxycarbonyl, alkanoylamino, aroylamino, carbamoyl, alkylcarbamoyl, dialkylcarbamoyl, arylcarbamoyl, aralkylcarbamoyl, alkylsulfonyl, alkylsulfinyl, arylsulfonyl, arylsulfinyl, aralkylsulfonyl, aralkylsulfinyl, or —NRR' where R and R' are independently hydrogen, alkyl, aryl, or aralkyl; and where α-amino acyl is a naturally occurring amino acid group selected from the group consisting of glycyl, alanyl, valyl, leucyl, isoleucyl, seryl, threonyl, phenylalanyl, tyrosyl, tryptophanyl, cysteyl, methionyl, prolyl, hydroxyprolyl, aspartyl, asparginyl, glutamyl, glutaminyl, histidyl, arginyl, ornithyl, and lysyl;

or a pharmaceutically acceptable salt thereof; provided that when G is alkanoyl, alkenoyl, or N-alkanoyl- or N-alkenoyl-D- or L-α-amino acyl, then n is 0; and provided further that at least one of A or B is X—G—(M-)$_n$—.

2. A compound of claim 1 wherein G is alkanoyl, alkenoyl, benzoyl, phenylalkanoyl, phenylalkenoyl, alkyl- or alkenylbenzoyl, alkyl- or alkenylphenylalkanoyl, alkyl- or alkenylphenylalkenoyl, or N-alkanoyl- or N-alkenoyl-D- or L-α-amino acyl.

3. A compound of claim 1 wherein A and B are independently X—G—M)$_n$—, and G is benzoyl, phenylalkanoyl, phenylalkenoyl, alkyl- or alkenylbenzoyl, alkyl- or alkenylphenylalkanoyl, alkyl- or alkenylphenylalkenoyl.

4. A compound of claim 1 wherein G is alkanoyl, alkenoyl, or N-alkanoyl-or N-alkenoyl-D- or L-α-amino acyl.

5. A compound of claim 4 wherein G is alkanoyl or alkenoyl.

6. A compound of claim 1 wherein X is

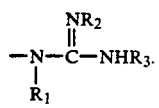

7. A compound of claim 5 wherein X is

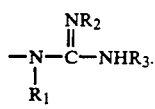

8. A pharmaceutical composition comprising a compound of claim 1 in an amount effective to inhibit thrombus formation in a mammal and a pharmaceutically acceptable carrier.

9. A compound of claim 1 which is (3R)-N-L-arginyl-N'-(8-guanidino)octanoyl-3,3-diaminopropionic acid or a pharmaceutically acceptable salt thereof.

10. A compound of claim 1 which is (3S)-N-L-arginyl-N'-(8-guanidino)octanoyl-3,3-diaminopropionic acid or a pharmaceutically acceptable salt thereof.

11. A compound of claim 1 which is (3R)-N-[N-[(5-guanidino)pentanoyl]-D-isoleucyl]-N'-(9-guanidino)nonanoyl-3,3-diaminopropionic acid or a pharmaceutically acceptable salt thereof.

12. A compound of claim 1 which is (3S)-N-[N-[(5-guanidino)pentanoyl]-D-isoleucyl]-N'-(9-guanidino)nonanoyl-3,3-diaminopropionic acid or a pharmaceutically acceptable salt thereof.

13. A compound of claim 1 which is (3R)-N-[N-[(5-guanidino)pentanoyl]-L-isoleucyl]-N'-(9-guanidino)nonanoyl-3,3-diaminopropionic acid or a pharmaceutically acceptable salt thereof.

14. A compound of claim 1 which is (3S)-N-[N-[(5-guanidino)pentanoyl]-L-isoleucyl]-N'-(9-guanidino)nonanoyl-3,3-diaminopropionic acid or a pharmaceutically acceptable salt thereof.

15. A compound of the formula

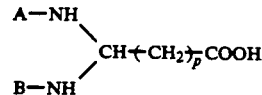

wherein:

A and B are independently alkanoyl, alkenoyl, or X—G— where

X is

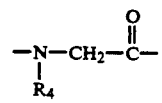

where $R_1$, $R_2$, and $R_3$, are independently hydrogen or alkyl;

G is alkanoyl, or alkenoyl; and p is 1, 2, or 3;

or a pharmaceutically acceptable salt thereof; provided that at least one of A or B is X—G—.

16. A compound according to claim 15 wherein A and B are independently X—G—.

17. A compound of claim 16 which is N,N'-bis-(8-guanidino)octanoyl-3,3-diaminopropionic acid or a pharmaceutically acceptable salt thereof.

18. A compound of claim 16 which is (3S)-N-(8-guanidino)octanoyl-N'-(9-guanidino)nonanoyl-3,3-diaminopropionic acid or a pharmaceutically acceptable salt thereof.

19. A compound of claim 16 which is N,N'-bis-(7-guanidino)heptanoyl-3,3-diaminopropionic acid or a pharmaceutically acceptable salt thereof.

20. A compound of claim 16 which is N,N'-bis-(9-guanidino)nonanoyl-3,3-diaminopropionic acid or a pharmaceutically acceptable salt thereof.

21. A compound of claim 16 which is (3S)-N-(7-guanidino)heptanoyl-N'-(9-guanidino)nonanoyl-3,3-diaminopropionic acid or a pharmaceutically acceptable salt thereof.

22. A compound of claim 16 which is (3S)-N-(7-guanidino)heptanoyl-N'-(8-guanidino)octanoyl-3,3-diaminopropionic acid or a pharmaceutically acceptable salt thereof.

23. A compound of claim 16 which is (3R)-N-(8-guanidino)octanoyl-N'(9-guanidino)nonanoyl-3,3-diaminopropionic acid or a pharmaceutically acceptable salt thereof.

24. A compound of claim 16 which is (3R)-N-(7-guanidino)heptanoyl-N'-(9-guanidino)nonanoyl-3,3-diaminopropionic acid or a pharmaceutically acceptable salt thereof.

25. A compound of claim 16 which is (3R)-N-(7-guanidino)heptanoyl-N'-(8-guanidino)octanoyl-3,3-diaminopropionic acid or a pharmaceutically acceptable salt thereof.

26. A compound of claim 15 which is (3R)-N-(8-guanidino)octanoyl-N'-(3-methyl)butanoyl-3,3- diaminopropionic acid or a pharmaceutically acceptable salt thereof.

27. A compound of claim 15 which is (3S)-N-(8-guanidino)octanoyl-N'-(3-methyl)butanoyl-3,3-diaminopropionic acid or a pharmaceutically acceptable salt thereof.

28. A compound of claim 15 which is N,N'-bis-(8-guanidino)octanoyl-4,4-diaminobutanoic acid.

* * * * *